(12) United States Patent
Nakaminami et al.

(10) Patent No.: US 7,646,474 B2
(45) Date of Patent: *Jan. 12, 2010

(54) MEASURING DEVICE, MEASURING APPARATUS AND METHOD OF MEASURING

(75) Inventors: Takahiro Nakaminami, Osaka (JP); Akihito Kamei, Kyoto (JP); Atsushi Fukunaga, Osaka (JP)

(73) Assignee: Panasonic Corporation, Osaka (JP)

( * ) Notice: Subject to any disclaimer, the term of this patent is extended or adjusted under 35 U.S.C. 154(b) by 120 days.

This patent is subject to a terminal disclaimer.

(21) Appl. No.: 11/995,473

(22) PCT Filed: Oct. 24, 2006

(86) PCT No.: PCT/JP2006/321147

§ 371 (c)(1),
(2), (4) Date: Jan. 11, 2008

(87) PCT Pub. No.: WO2007/049607

PCT Pub. Date: May 3, 2007

(65) Prior Publication Data

US 2009/0219514 A1   Sep. 3, 2009

(30) Foreign Application Priority Data

Oct. 28, 2005 (JP) .............................. 2005-314963
Nov. 2, 2005 (JP) .............................. 2005-319714

(51) Int. Cl.
*G01N 21/00* (2006.01)

(52) U.S. Cl. ....................................................... 356/72

(58) Field of Classification Search ................... 356/72, 356/73
See application file for complete search history.

(56) References Cited

U.S. PATENT DOCUMENTS

| 3,811,841 A * | 5/1974 | Kassel .......................... 422/82 |
| 5,084,397 A | 1/1992 | Siddons et al. |
| 5,141,868 A | 8/1992 | Shanks et al. |
| 5,162,237 A | 11/1992 | Messenger et al. |
| 5,286,454 A | 2/1994 | Nilsson et al. |
| 2004/0191119 A1 | 9/2004 | Zanzucchi et al. |

FOREIGN PATENT DOCUMENTS

EP   0 545 284 A   6/1993

(Continued)

OTHER PUBLICATIONS

European Search Report issued in European Patent Application No. EP 06822127 dated Jan. 29, 2009.

*Primary Examiner*—Tarifur Chowdhury
*Assistant Examiner*—Abdullahi Nur
(74) *Attorney, Agent, or Firm*—McDermott Will & Emery LLP

(57) ABSTRACT

A measuring device for analyzing an analyte contained in a sample. The device includes a hollow housing, a sample holding part provided inside the housing for holding the sample, a sample supply inlet provided for the housing so as to communicate with the sample holding part, an optical measurement part provided for the sample holding part for making an optical measurement, a reagent holding part provided for the sample holding part for holding a reagent for the optical measurement, and at least one electrode provided on an outer surface of the housing.

5 Claims, 14 Drawing Sheets

FOREIGN PATENT DOCUMENTS

| | | |
|---|---|---|
| FR | 2 611 906 A | 9/1988 |
| JP | 03-245049 | 10/1991 |
| JP | 05-079989 | 3/1993 |
| JP | 07-209189 | 8/1995 |
| JP | 07-248310 | 9/1995 |
| JP | 09-127126 | 5/1997 |
| WO | WO 90/13016 | 11/1990 |
| WO | WO 2005/108960 A1 | 11/2005 |

* cited by examiner

MEASURING DEVICE, MEASURING APPARATUS AND METHOD OF MEASURING

RELATED APPLICATIONS

This application is the U.S. National Phase under 35 U.S.C. § 371 of International Application No. PCT/JP2006/321147, filed on Oct. 24, 2006, which in turn claims the benefit of Japanese Application No. 2005-314963, filed on Oct. 28, 2005, and Japanese Application No. 2005-319714, filed on Nov. 2, 2005, the disclosures of which Applications are incorporated by reference herein.

TECHNICAL FIELD

The present invention relates to a measuring device, a measuring apparatus, and a measuring method for analyzing an analyte contained in a sample.

BACKGROUND ART

Measuring instruments conventionally used in the field of clinical tests are mainly large-sized automated devices and POCT (Point of Care Testing) devices.

Large-sized automated devices are installed in hospital clinical laboratories and commercial clinical laboratories and capable of testing samples of many patients for a large number of items (e.g., see Patent Document 1). For example, a large-sized automated device of Hitachi 7170 is capable of performing 800 tests per hour for up to 36 items. Thus, they contribute to higher test efficiency and are equipment suited for hospitals with a large number of examinees.

Meanwhile, POCT devices refer to devices used in clinical tests that are conducted in medical settings other than hospital laboratories and test centers, and include devices for use in home healthcare (e.g., see Patent Document 2 and Patent Document 3). Such examples include blood sugar sensors, pregnancy test drugs, ovulation test drugs, and HbA1c/microalbumin analyzers (e.g., DCA 2000 available from Bayer AG). These POCT devices are inferior in versatility to large-sized automated devices, but are capable of focusing on a marker substance specific to a disease and measuring the marker substance in a simple and prompt manner. They are thus effective for screening and monitoring examinees. Also, POCT devices are small and portable, can be introduced at low costs, and can be used by anyone without requiring particular expertise in operation.

Currently, there are many items measured in clinical tests. When a body fluid such as urine is used as a sample, the measurement methods are roughly divided into optical measurement type and electrochemical measurement type. The above-described conventional large-sized automated devices and POCT devices use either type of measurements for making measurements.

Recently, swelling medical expenses and an increasing number of patients with life-style related diseases have been imposing a burden on medical economy, thereby necessitating a reduction in medical expenses and suppression of increasing patients with lifestyle-related diseases. One fundamental solution of such problem could be Evidence Based-medical (EBM). EBM allows objective management of medical care according to individual patients' needs, and it is expected that practicing preventive healthcare will lead particularly to a reduction in the number of patients with lifestyle-related diseases, etc.

To establish and practice EBM, test information obtained from clinical tests is essential. Test information in EBM includes test results and solutions for patients based on the test results. As used herein, "solutions for patients" refer to guidance on lifestyle such as diet control, treatment by medication, and the like. That is, in EBM, tests are conducted in order to allow those who are to receive medical care to "find their problems" and "make a decision on courses of treatment". In order to provide safer and better solutions in EBM, it is necessary to clearly present problems to those who are to receive medical care. Hence, in clinical tests, it has become important to obtain the test results of a plurality of interrelated test items easily and promptly.

The above-described conventional large-sized automated devices are versatile and capable of testing a large number of items regardless of whether or not they are related to a disease. However, since such devices have complicated structures, they are difficult to operate for those without expertise. Further, there is a problem in that it takes long time to obtain a test result so that it takes long time to feed back the result to the examinee. Also, although the POCT devices are superior in operability and capable of easy and prompt tests, they are unable to test a plurality of items, since they are measurement devices designed specifically for markers that are related to specific diseases.

Thus, there has been proposed a device for use in biochemical or clinical tests, which includes a cavity into which a liquid sample flows by capillary action. The cavity includes an electrode structure for measuring at least one electrical characteristic of the sample, and a reagent such as an antibody or enzyme capable of being released into the cavity. A wall of the cavity is transparent so that the cavity contents can be optically measured (e.g., Patent Document 4).

Patent Document 1: Japanese Laid-Open Patent Publication No. Hei 09-127126
Patent Document 2: Japanese Laid-Open Patent Publication No. Hei 07-248310
Patent Document 3: Japanese Laid-Open Patent Publication No. Hei 03-046566
Patent Document 4: U.S. Pat. No. 5,141,868

DISCLOSURE OF THE INVENTION

Problem to be Solved by the Invention

However, the structure of the device of Patent Document 4 has a problem in that the reagent used for the optical measurement dissolves in the sample supplied in the cavity and reaches the electrode structure, thereby adversely affecting the measurement of the electrical characteristic by the electrode structure.

Therefore, in view of the conventional problems as described above, an object of the present invention is to provide a measuring device, a measuring apparatus, and a measuring method capable of measuring a plurality of test items promptly and accurately by performing optical and electrochemical measurements of a sample using a simple configuration.

Means for Solving the Problem

In order to solve the above-mentioned conventional problems, the present invention provides a measuring device for analyzing an analyte contained in a sample. The device includes: a hollow housing; a sample holding part provided inside the housing for holding the sample; a sample supply inlet provided for the housing so as to communicate with the sample holding part; an optical measurement part provided for the sample holding part for making an optical measurement; a reagent holding part provided for the sample holding part for holding a reagent for the optical measurement; and at least one electrode provided on an outer surface of the housing.

The present invention also provides a measuring apparatus including: a measuring-device mounting part for mounting the above-described measuring device; a light source for emitting light that will enter the optical measurement part of the measuring device; a light receiver for receiving light that has exited from the optical measurement part; a voltage applying unit for applying a voltage to the electrodes; an electrical signal measuring unit for measuring an electrical signal from the electrodes; and a processor for detecting or quantifying the analyte contained in the sample based on at least one of the light received by the light receiver and the electrical signal measured by the electrical signal measuring unit.

The present invention also provides a method for measuring a first analyte and a second analyte contained in a sample by using the above-described measuring device. The method includes the steps of: (A) applying a voltage to the electrodes of the measuring device; (B) measuring an electrical signal from the electrodes; (C) sucking the sample into the sample holding part through the sample supply inlet; (D) detecting or quantifying the second analyte based on the electrical signal measured in the step (B); (E) irradiating the sample held in the sample holding part with light through the optical measurement part; (F) measuring light which has originated from the irradiation of light and exited from the sample holding part through the optical measurement part; and (G) detecting or quantifying the first analyte based on the light measured in the step (F).

EFFECTS OF THE INVENTION

The present invention can provide a measuring device, a measuring apparatus, and a measuring method capable of measuring a plurality of test items promptly and accurately by performing optical and electrochemical measurements of a sample.

BEST MODE FOR CARRYING OUT THE INVENTION

Figure 1:
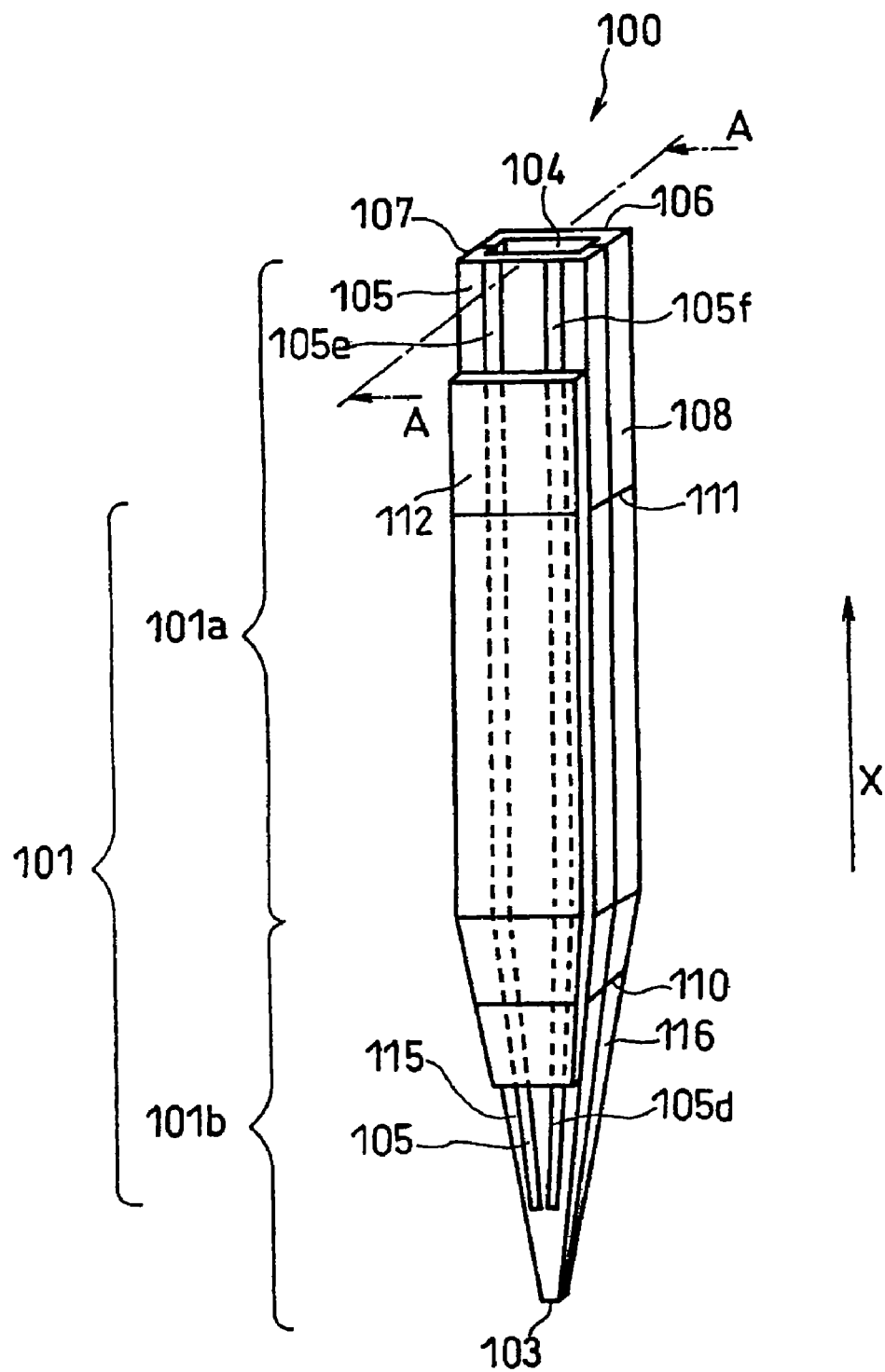
FIG. 1 is a perspective view showing the structure of one embodiment of a measuring device according to the present invention.

The measuring device of the present invention includes a hollow housing; a sample holding part provided inside the housing for holding the sample; a sample supply inlet provided for the housing so as to communicate with the sample holding part; an optical measurement part provided for the sample holding part for making an optical measurement; a reagent holding part provided for the sample holding part for holding a reagent for the optical measurement; and at least one electrode provided on an outer surface of the housing.

With this configuration, by supplying a sample to the sample holding part once, it is possible to perform optical and electrochemical measurements of the sample by using one measuring device. By carrying the reagent on the inner surface of the housing, disposing the at least one electrode on the outer surface of the housing, and bringing the sample into contact with the at least one electrode on the outer surface, it is possible to perform optical and electrochemical measurements. Hence, the reagent necessary for the optical measurement is prevented from diffusing to the electrode and affecting the electrochemical measurement, so that a plurality of test items can be measured promptly and correctly.

The optical measurement part preferably has a light entrance for allowing light to enter the sample holding part, and a light exit for allowing light to exit from the sample holding part.

The light entrance and the light exit are preferably made of an optically transparent material or a material that does not substantially absorb visible light. Such examples include quartz, glass, polystyrene, and polymethyl methacrylate. When the sensor is made disposable, polystyrene is preferable in terms of costs.

Also, the at least one electrode preferably includes a pair of electrodes. With this configuration, for example, by measuring the conductivity of a sample, the concentration of a salt contained in the sample can be obtained.

Preferable materials for the electrode are those containing at least one of gold, platinum, palladium, alloys thereof, mixtures thereof, and carbon. Alternatively, indium tin oxide (ITO) is preferable as a transparent electrode. Since these materials are chemically and electrochemically stable, they can realize stable measurements. In the case of measuring the conductivity of a sample, it is also possible to use copper, zinc, nickel, an alloy or mixture thereof, and stainless steel, since no electrochemical reaction is involved.

Also, the electrode is preferably an electrode for measuring the concentration of a specific compound or ion contained in a sample. With this configuration, the concentration of a specific compound or ion in a sample can be obtained. For example, by using a glass electrode or the like, the concentration of sodium ion can be measured.

Further, the electrode is preferably an electrode having a membrane sensitive to a specific ion contained in a sample (ion-sensitive membrane). With this configuration, the concentration of a specific ion in a sample can be obtained.

The ion-sensitive membrane can be one having a function of selectively allowing one of such ions as sodium ion, potassium ion, lithium ion, magnesium ion, calcium ion, chloride ion, ammonium ion, and hydrogen ion to pass through.

The compound forming the ion-sensitive membrane can be a known compound suitable for the ion to be passed through. For example, the following ion-selective inclusion compounds can be used: for sodium ion, bis[(12-crown-4)methyl] 2,2-dibenzomalonate etc.; for potassium ion, bis[(benzo15-crown-5)4-methyl]pimelate etc.; for lithium ion, phosphododecyl-14-crown-4 etc.; for magnesium ion, 4,13-bis[N-(1-adamantyl)carbamoylacetyl]-8-tetradecyl-1,7,10,16-tetraoxa-4,13-diazacyclooctadecane etc.; for calcium ion, 4,16-bis(N-octadecylcarbamoyl)-3-octbutyryl-1,7,10,13,19-pentaoxa-4,16-diazacyclohenicosane etc.; for chloride ion, 2,7-di-tert-butyl-9,9-dimethyl-4,5-bis(N-n-butylthioureylene)xanthene etc.; and for ammonium ion, 2,6,13,16,23,26-hexaoxaheptacyclo[25.4.4.4$^{7,12}$.4$^{17,22}$.0$^{1,17}$.0$^{7,12}$.0$^{17,22}$] tritetracontane etc. They are available, for example, from DOJINDO LABORATORIES as commercial products.

An example of methods of forming the ion-sensitive membrane on the electrode is a method of dissolving such an inclusion compound, a plasticizer, an anion remover, and a polymer compound such as PVC in an organic solvent, applying the resultant mixture solution onto the electrode, and drying it by air or the like.

The electrode may be a field-effect transistor (FET) electrode formed of silicon or the like. Also, a reference electrode with stable potential, for example, a Ag/AgCl or saturated calomel electrode is preferably used as one electrode or a third electrode in combination with other electrode.

Also, an enzyme is preferably carried on the electrode. Since an enzyme highly selectively catalyzes the reaction of a specific compound, a highly selective measurement of a specific compound in a sample can be realized. A known optimum enzyme in terms of selectivity and reactivity is used depending on the compound to be measured.

Examples of enzymes include glucose oxidase, glucose dehydrogenase, alcohol oxidase, cholesterol oxidase, and sarcosine oxidase. These enzymes are commercially available. Also, the use of cholesterol esterase in combination with cholesterol oxidase allows detection of ester-type cholesterol. Alternatively, the use of creatininase and creatinase in combination with sarcosine oxidase permits quantification of creatinine, creatine, or sarcosine.

In the present invention, the enzyme is preferably immobilized to the electrode without dissolving in the sample. With this configuration, even if there are variations in the amount of sample, accurate measurements are possible.

Also, if necessary, an electron mediator allowing electron transfer between the enzyme and the electrode, for example, ferri/ferrocyanide ion, a ferrocene derivative, a ruthenium complex, an osmium complex, or a quinone derivative may be used. When the enzyme is immobilized to the electrode, it is more preferable to immobilize the electron mediator together.

In the measuring device of the present invention, the reagent preferably includes an enzyme or antibody. The reagent is preferably disposed such that it is placed in a dry state in the sample holding part and dissolved in a sample when the sample is supplied to the sample holding part.

For example, a porous carrier made of glass fiber, filter paper, etc., is impregnated with a solution of the reagent and dried to carry the reagent on the carrier, and the carrier is disposed in the sample holding part. Also, the reagent may be disposed by directly applying a solution of the reagent to a wall face of the sample holding part and drying it.

An antibody as a reagent can be produced by known methods and is thus advantageous in that the reagent can be easily prepared. For example, by immunizing a mouse, a rabbit or the like using a protein such as albumin or a hormone such as hCG or LH as an antigen, an antibody to the antigen can be obtained.

Examples of antibodies include an antibody to a protein contained in urine, such as albumin, and an antibody to a hormone contained in urine, such as hCG or LH. If necessary, a compound which promotes the coagulation reaction between an antigen and an antibody, such as polyethylene glycol, may be provided in the vicinity of the antibody in the measuring device.

An enzyme as a regent highly selectively catalyzes the reaction of a specific compound, and hence a highly selective measurement of a specific compound in a sample can be realized. A known optimum enzyme in terms of selectivity and reactivity is used depending on the compound to be measured.

Examples of enzymes include glucose oxidase, glucose dehydrogenase, alcohol oxidase, cholesterol oxidase, sarcosine oxidase, and other oxidoreductases. In this case, by providing a colorant or colorant source whose color changes or disappears as a result of enzyme reaction together with the enzyme, the optical measurement is stabilized. These enzymes are commercially available. Also, the use of cholesterol esterase in combination with cholesterol oxidase permits detection of ester-type cholesterol. Also, the use of creatininase and creatinase in combination with sarcosine oxidase allows quantification of creatinine, creatine, or sarcosine.

The housing of the measuring device of the present invention preferably has a first reference line that indicates a position up to which the housing is to be immersed in the sample when the measuring device is immersed in the sample. With this configuration, the user can easily find up to which part of the measuring device the user should immerse the measuring device in the sample.

The first reference line is preferably provided such that at least a part of the electrode is positioned between the sample supply inlet and the first reference line. With this configuration, when the measuring device is immersed in the sample up to the position of the first reference line, it is possible to ensure that at least a part of the electrode comes into contact with the sample.

Also, the housing of the measuring device of the present invention preferably has a second reference line that indicates the amount of the sample to be supplied to the housing. With this configuration, when the sample is supplied to the sample holding part, it is possible to check whether a predetermined amount of sample is held in the sample holding part.

Also, preferably, the measuring device of the present invention further includes conductive members disposed on the outer surface of the housing and a cover that covers the conductive members so as to expose a part of each of the conductive members, so that the parts of the conductive members exposed without being covered by the cover (the above-mentioned part) function as the electrodes. That is, the exposed parts correspond to the electrodes. With this configuration, since the electrode area can be defined by using the cover, highly quantitative electrochemical measurements are possible. Also, each of the conductive members may have a plurality of parts that are exposed without being covered by the cover, so that at least one of the plurality of parts can function as the electrode.

Also, the measuring apparatus of the present invention includes a measuring-device mounting part for mounting the above-described measuring device; a light source for emitting light that will enter the optical measurement part of the measuring device; a light receiver for receiving light that has exited from the optical measurement part; a voltage applying unit for applying a voltage to the electrodes; an electrical signal measuring unit for measuring an electrical signal from the electrodes; and a processor for detecting or quantifying the analyte contained in the sample based on at least one of the light received by the light receiver and the electrical signal measured by the electrical signal measuring unit.

Preferably, the measuring device is detachably mounted in the measuring apparatus. Also, the measuring device is preferably disposable.

Also, it is preferable for the measuring apparatus of the present invention to further include a suction unit for supplying the sample by suction to the sample holding part of the measuring device mounted in the measuring-device mounting part.

It is thus preferable for the measuring device of the present invention to further include a sucking port for sucking the sample into the sample holding part from the sample supply inlet. With this configuration, by mounting the measuring device such that the sucking port of the measuring device is connected to the measuring-device mounting part, and by using the suction unit, a sample can be easily supplied to the sample holding part of the measuring device from the sample supply inlet.

The sucking unit may be manual or automatic and may be, for example, a piston mechanism such as a conventional syringe or dispenser.

The piston of such a piston mechanism may be operated manually or automatically, but automatic operation is preferable since it can reduce the workload of the operator. Automation methods include a method of operating the piston by means of a motor. The motor may be a stepper motor, a DC motor, etc.

A stepper motor is a motor that rotates by a particular rotation angle per input pulse signal and the rotation angle can be determined by the number of pulses. Thus, it does not need an encoder for positioning. That is, the operation distance of the piston can be controlled based on the number of input pulses.

The rotational motion of the motor is converted to linear motion by using, for example, a linear motion mechanism consisting of a gear mechanism combined with male and female threads, to operate the piston. The rotational motion of a DC motor is also converted to linear motion in the same manner, but a DC motor needs an encoder that detects the rotational position of the motor in order to control the operation distance of the piston. There is also a linear stepper motor. In the case of this type of motor, the motor contains a linear motion mechanism consisting of combined male and female threads, and a movable bar moves linearly depending on the number of input pulses. Thus, the piston can be directly connected to this bar, which makes the structure simple.

Also, the measuring method of the present invention is a method for measuring a first analyte and a second analyte contained in a sample by using the above-described measuring device. The method includes the steps of: (A) applying a voltage to the electrodes of the measuring device; (B) measuring an electrical signal from the electrode; (C) sucking the sample into the sample holding part through the sample supply inlet; (D) detecting or quantifying the second analyte based on the electrical signal measured in the step (B); (E) irradiating the sample held in the sample holding part with light through the optical measurement part; (F) measuring light which has originated from the irradiation of light and exited from the sample holding part through the optical measurement part; and (G) detecting or quantifying the first analyte based on the light measured in the step (F).

In the step (A), with the measuring device being immersed in the sample such that the sample and the electrodes are in contact with each other, the application of the voltage to the electrodes may be started. Alternatively, after the application of the voltage to the electrodes is started, and with the voltage being applied, the measuring device may be immersed in the sample such that the sample and the electrodes are in contact with each other.

It is preferable to detect a change in the electrical signal in the step (B) and automatically perform the step (C) based on the detection.

In this case, by detecting a change in the electrical signal in the electrodes, it is possible to detect that the sample supply inlet of the measuring device has been immersed in the sample. It is therefore possible to prevent the sample from being mistakenly sucked before the sample supply inlet is immersed in the sample.

It is also preferable to perform the step (B) while performing the step (C), detect a change in the electrical signal in the step (B), and automatically stop the sucking of the sample based on the detection. In this case, by detecting a change in the electrical signal in the electrodes while sucking the sample, it is possible to detect that the measuring device has been pulled out of the sample. By automatically stopping the sucking of the sample based on the detection, it is possible to prevent the sucking of the sample from being continued when the sample is away from the sample supply inlet.

Further, based on one of the quantification result of the first analyte and the quantification result of the second analyte, the other quantification result is preferably corrected.

In this case, by measuring a plurality of interrelated test items, the accuracy of measurement results can be enhanced. Exemplary combinations of a first analyte and a second analyte include a combination of blood sugar and HbA1c, a combination of a urine component such as albumin or urine sugar and creatinine.

Examples of samples used in the present invention include body fluids such as serum, plasma, blood, urine, interstitial fluid, and lymph, and liquid samples such as supernatant fluid of a culture medium. Also, a mixture of a body fluid and a reagent which reacts with a specific component in the body fluid, such as an enzyme, antibody, or colorant, may be supplied to the measuring device as the sample.

Among them, urine is preferable as the sample. When the sample is urine, daily health management can be made at home in a noninvasive manner.

Examples of the first analyte include albumin, hCG, LH, CRP, and IgG. Also, examples of the second analyte include sodium ion, potassium ion, lithium ion, magnesium ion, calcium ion, chloride ion, ammonium ion, hydrogen ion, and glucose.

In a qualitative analysis of urine, which is conducted in an initial stage of health management, twelve items, namely pH, specific gravity, protein, sugar, occult blood, ketone body, bilirubin, urobilinogen, nitrite, leukocyte, ascorbic acid, amylase, and salt are tested. Also, microalbumin is tested to assess kidney function, and hormones such as hCG and LH are tested as markers for pregnancy/ovulation tests etc.

Among these test items, protein, microalbumin, and hormones such as hCG and LH are suited for optical measurements based on antigen-antibody reaction. Examples of optical measurements based on antigen-antibody reaction include measurements of turbidity in a sample caused by antigen-antibody reaction, such as nephelometric immunoassay, turbidimetric immunoassay, and latex agglutination immunoassay.

Meanwhile, salts (sodium ion, potassium ion), pH, sugars, etc. in urine are mainly measured electrochemically. In particular, salts and sugars in urine reflect lifestyle such as meals and are thus important information for proposing healthcare solutions.

Salts and pH affect antigen-antibody reaction. For example, at high salt concentrations, antigen-antibody reaction exhibits high degree of dissociation and the amount of reaction decreases. As a result, negative measurement errors are induced. Since salts in urine and pH thereof are subject to circadian variation, non-circadian variation, and individual differences, it is difficult to predict errors. However, errors in the measurement of antigen concentration can be corrected by determining the level of salt or pH by electrochemical measurement, and referring to data on the relation between outgoing light intensity and antigen concentration at various salt concentrations and pH values as a calibration curve in optical measurement.

1. Measuring Device

With reference to drawings, one preferable embodiment of the measuring device of the present invention is described in details. In the following description of this embodiment, the sample is urine, the first analyte is human albumin, and the second analyte is glucose.

Figure 2:
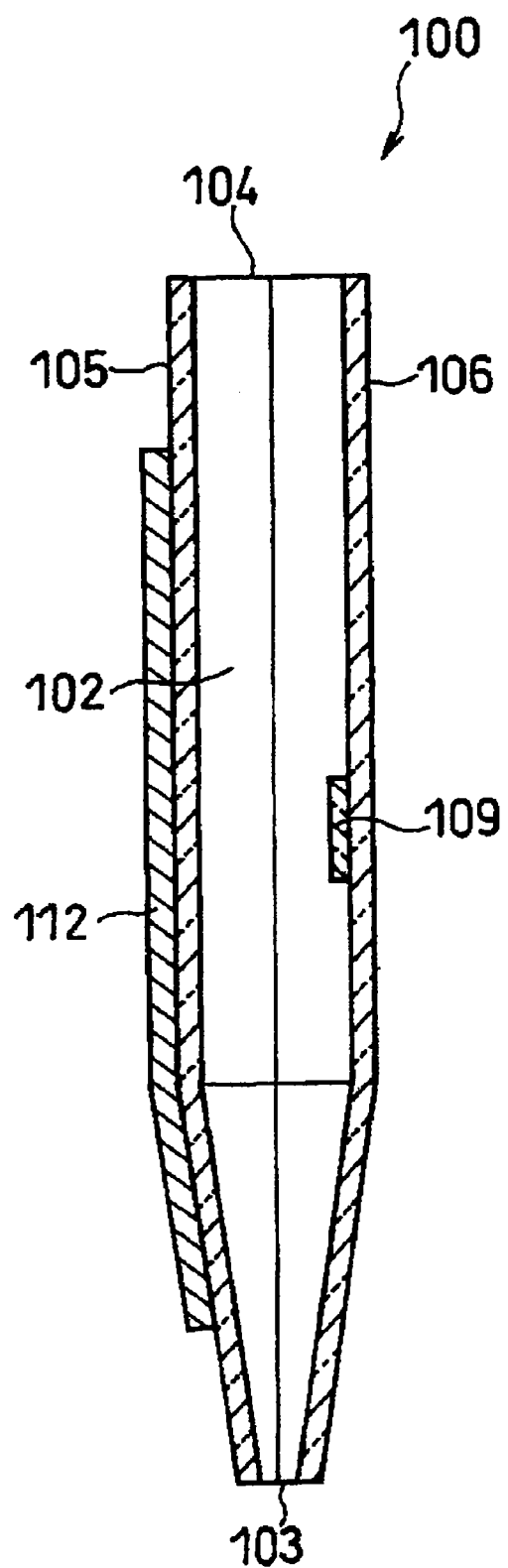
FIG. 2 is a cross-sectional view of the A-A part of FIG. 1.

First, referring to FIG. 1, the structure of the measuring device according to this embodiment is described. FIG. 1 is a perspective view of a measuring device according to this embodiment, and FIG. 2 is a cross-sectional view of the A-A part of FIG. 1.

A measuring device 100 of this embodiment includes a hollow housing 101 made of transparent polystyrene. Both ends of the housing 101 are open, and inside the housing 101 is a space. The space serves as a sample holding part 102.

Also, one open end of the space serving as the sample holding part 102 serves as a sample supply inlet 103, while the other open end serves as a sucking port 104.

More specifically, the housing 101 has a hollow quadrangular prismatic section 101a and a hollow quadrangular pyramidal section 101b. One end of the hollow quadrangular prismatic section 101a is provided with the sucking port 104, while the other end of the hollow quadrangular prismatic section 101a is integrated with the hollow quadrangular pyramidal section 101b. The end of the hollow quadrangular pyramidal section 101b opposite to the hollow quadrangular prismatic section 101a is provided with the sample supply inlet 103.

Of the four faces constituting the exterior of the hollow quadrangular prismatic section 101a of the housing 101, a first face 105 is provided with a pair of conductive parts. These conductive parts extend to a first face 115 of the hollow quadrangular pyramidal section 101b adjacent to the first face 105 of the hollow quadrangular prismatic section 101a. An insulating resin cover 112 is disposed on the conductive parts so as to expose both ends of the conductive parts. The ends of the conductive parts on the first face 105 of the hollow quadrangular prismatic section 101a serve as connecting parts 105e and 105f, while the ends thereof on the first face 115 of the hollow quadrangular pyramidal section 101b serve as electrodes 105c and 105d, respectively.

Of the remaining three faces of the exterior of the hollow quadrangular prismatic section 101a, a second face 107 and a third face 108, which are on opposing sides of the first face 105, serve as a light entrance (hereinafter also referred to as "light entrance 107") and a light exit (hereinafter also referred to as "light exit 108"), respectively. The light entrance comprising the second face 107 and the light exit comprising the third face 108 correspond to the optical measurement part of this embodiment.

Of the inner walls surrounding the sample holding part 102, the inner wall of a fourth face 106 of the hollow quadrangular prismatic section 101a is provided with a reagent holding part 109.

When the measuring device 100 according to this embodiment is used, a part of the measuring device 100 is immersed in, for example, urine collected in a container, and the urine is supplied to the sample holding part 102 by sucking air in the sample holding part 102 from the sucking port 104 by using a measuring apparatus, as described later.

Thus, near the end of the cover 112 on the sample supply inlet 103 side, there is provided a first reference line 110 that indicates a position up to which the measuring device 100 is to be immersed in the sample. The first reference line 110 allows the user to easily find up to which part of the measuring device the user should immerse the measuring device into the sample. When the measuring device is immersed in the sample up to the first reference line 110, it is possible to ensure that the whole electrodes 105c and 105 can be immersed, thereby enabling accurate electrochemical measurements.

Also, between the first reference line 110 and the sucking port 104 of the housing 101, there is provided a second reference line 111 which indicates the amount of sample to be supplied to the sample holding part 102. In supplying the sample to the sample holding part, the second reference line 111 allows the user to check whether a predetermined amount of sample is held in the sample holding part, thereby enabling more reliable measurements.

The thickness and shape of the first reference line 110 and the second reference line 111 are not particularly limited as long as they are viewable. In FIG. 1, the first reference line 110 is provided only on the first face 115 and the third face 116 of the hollow quadrangular pyramidal section 101b, and the second reference line 111 is provided only on the first face 105 and the third face 108 of the hollow quadrangular prismatic section 101a; however, the reference lines may be provided around the whole perimeter of the housing 101.

The first reference line 110 and the second reference line 111 may be provided, for example, by printing on the surface of the housing 101 or may be provided by forming a groove or rib.

Figure 3:
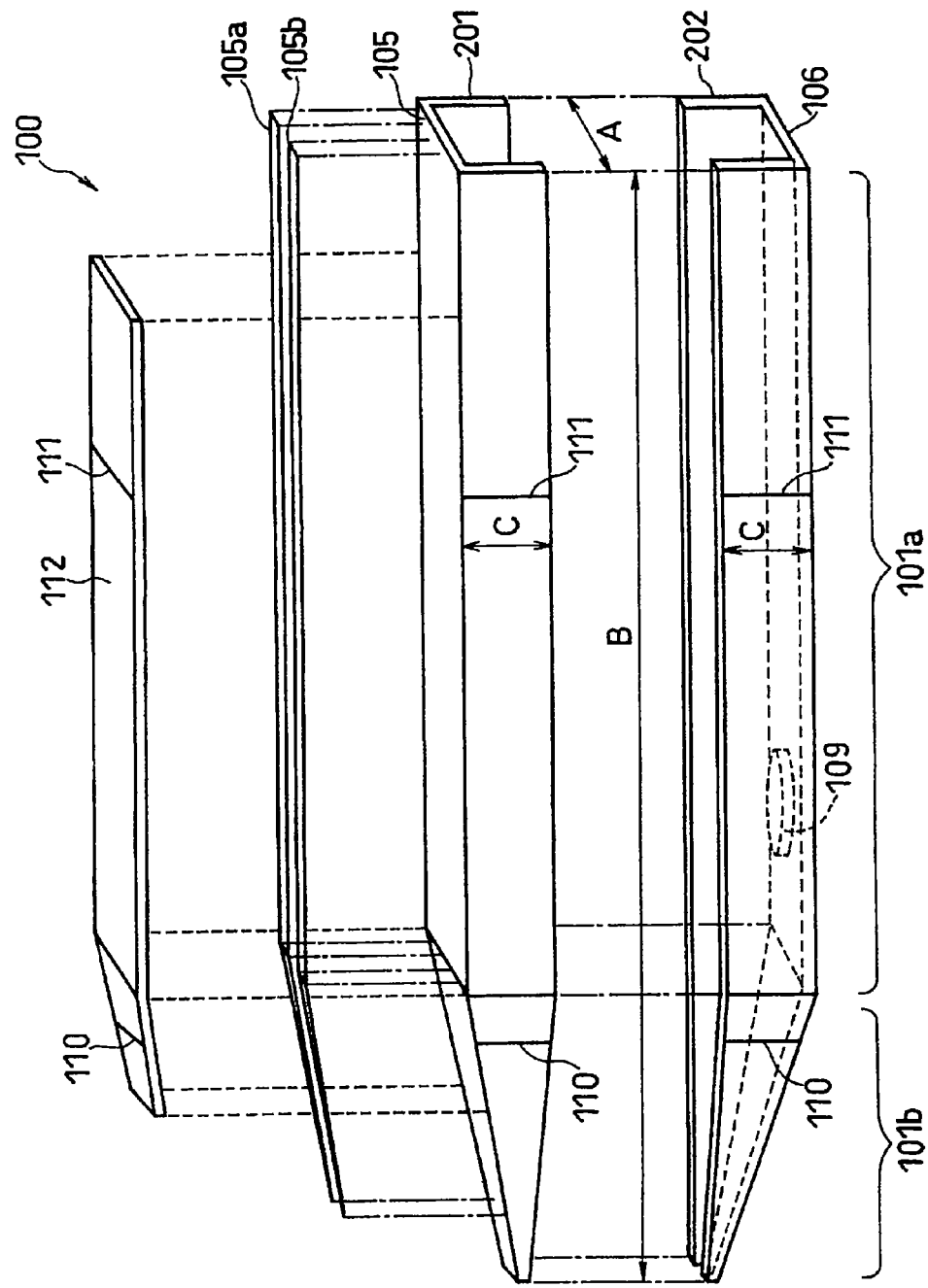
FIG. 3 is an exploded perspective view of the measuring device 100 of the present invention illustrated in FIG. 1.

Referring now to FIG. 3, the method for producing the measuring device of this embodiment is described. FIG. 3 is an exploded perspective view of the measuring device according to this embodiment.

A first member 201 and a second member 202, which form the measuring device 100, are made of transparent polystyrene and have a recess. The first member 201 and the second member 202 are combined together to form the housing having the hollow quadrangular prismatic section 101a and the hollow quadrangular pyramidal section 101b.

The first member 201 and the second member 202 can be obtained by molding using a mold. Known resin molding techniques may be used for molding. While the dimensions of the first member 201 and the second member 202 can be adjusted as appropriate, for example, the width A is 10 mm, the length B 84 mm, and the height C 6 mm.

Also, the first reference line 110 and the second reference line 111 of this embodiment can be formed by printing as described above; however, they can be easily formed by molding the first member 201 using a mold that has portions corresponding to grooves or ribs which constitute the first reference line 110 and the second reference line 111. In the case of printing, the first reference line 110 and the second reference line 111 can be formed after the production of the first member 201, the production of the housing 101, or the production of the conductive parts 105a and 105b.

Next, the reagent holding part 109 is formed on the bottom of the recess of the second member 202, i.e., on the inner wall of the fourth face 106.

For example, an antibody to human albumin is used as a reagent for optical measurement, and a certain amount of an aqueous solution of the antibody is applied to the bottom of the recess of the second member 202 by dropping it with a microsyringe, etc. This is then allowed to stand in an environment from room temperature to about 30° C. to evaporate the water. In this way, the reagent can be carried thereon in a dry state. For example, the above-mentioned antibody aqueous solution with a concentration of 8 mg/dL may be dropped in an amount of 0.7 mL onto an area of 5 $cm^2$.

The concentration and amount of the aqueous solution containing the reagent to be applied can be selected appropriately, according to the characteristics of the device required and the space restrictions on the formation position on the second member 202. Also, the area and position of the reagent holding part on the second member 202 can be selected appropriately in view of the solubility of the reagent in the sample, the position of the optical measurement part, etc.

The antibody to human albumin can be obtained by conventional methods. For example, an anti-human albumin antibody can be obtained by purifying an antiserum of a rabbit immunized with human albumin by protein A column chromatography and dialyzing it with a dialysis tube.

Meanwhile, the pair of conductive parts 105a and 105b is provided on the outer surface of the first member 201. The conductive parts 105a and 105b are mainly provided on the first face 105 of the hollow quadrangular prismatic section 101a and extend to the first face 115 of the hollow quadrangular pyramidal section 102b adjacent to the first face 105.

These conductive parts 105a and 105b can be formed by placing an acrylic resin mask with openings of the same shape as the conductive parts 105a and 105b on the outer surface of the first member 201, sputtering gold over the mask, and removing the mask. Instead of sputtering, vapor deposition may also be used in the same procedure.

While the dimensions of the conductive parts 105a and 105b are not particularly limited, for example, the width can be approximately 2 mm, the length approximately 80 mm, and the thickness approximately 5 µm. In order to define the size (length) of the electrodes 105c and 105d and the connecting parts 105e and 105f, the insulating resin cover 112 is attached to the conductive parts 105a and 105b so as to expose both ends of the conductive parts 105a and 105b. The cover 112 can be, for example, a PET film of approximately 10 mm in width, approximately 60 mm in length, and approximately 0.1 mm in thickness, with an acrylic adhesive applied thereto. The cover 112 is disposed such that the length of the electrodes and the cover is, for example, 10 mm.

The material, area, thickness, shape, position, etc. of the conductive parts, the electrodes, and the connecting parts and the number (number of pairs) thereof can be adjusted as appropriate in view of the characteristics of the device required, the position of the optical measurement part, etc.

Also, glucose oxidase, which is an enzyme, and an osmium complex, which is an electron mediator, are immobilized to the surface of the electrodes 105c and 105d of this embodiment by using a known method. For example, a solution of polyvinylimidazole combined with osmium bis(bipyridine) chloride by coordinate bonding is mixed with a solution of glucose oxidase, and the resultant solution is applied onto the electrodes 105c and 105d. This solution on the electrodes 105c and 105d is then mixed with polyethylene glycol diglycidyl ether, which is an amine crosslinking agent. After a stand-by of approximately one hour, the surface of the electrodes 105c and 105d is washed with distilled water.

The first member 201 and the second member 202 obtained in the above manner are bonded together in the positional relation as shown by the broken line in FIG. 3, to fabricate the measuring device 100. The measuring device 100 is fabricated by applying an adhesive such as epoxy resin to the joint between the first member 201 and the second member 202, bonding the first member 201 and the second member 202 together, allowing them to stand, and drying them.

It is also possible to join the first member 201 and the second member 102 together without applying an adhesive, and thermally or ultrasonically welding the joints between the first member 201 and the second member 102 by using a commercially available welding machine. In this way, the measuring device 100 illustrated in FIGS. 1 and 2 can be produced.

2. Measuring Apparatus

Figure 4:
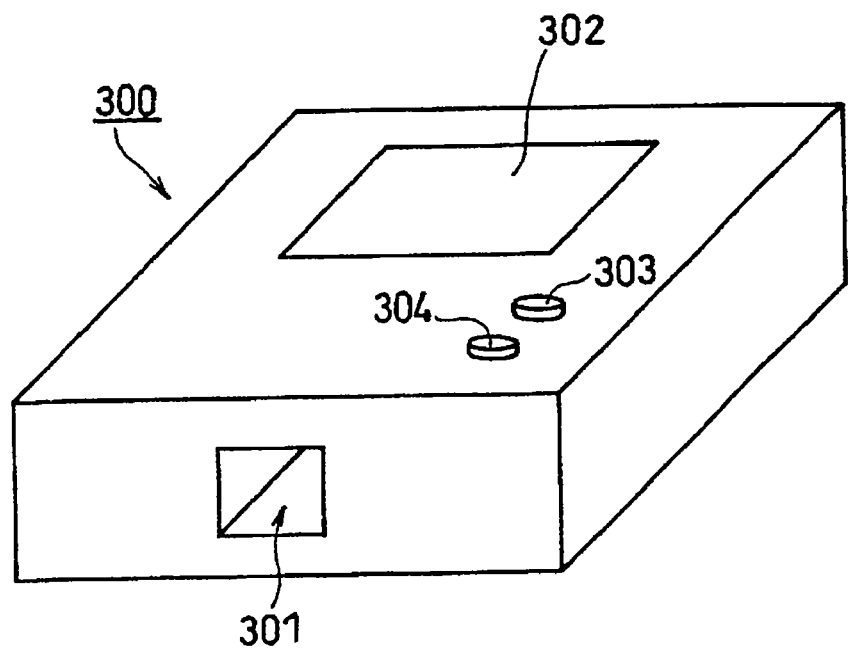
FIG. 4 is a perspective view showing the structure of one embodiment of a measuring apparatus according to the present invention.
Figure 5:
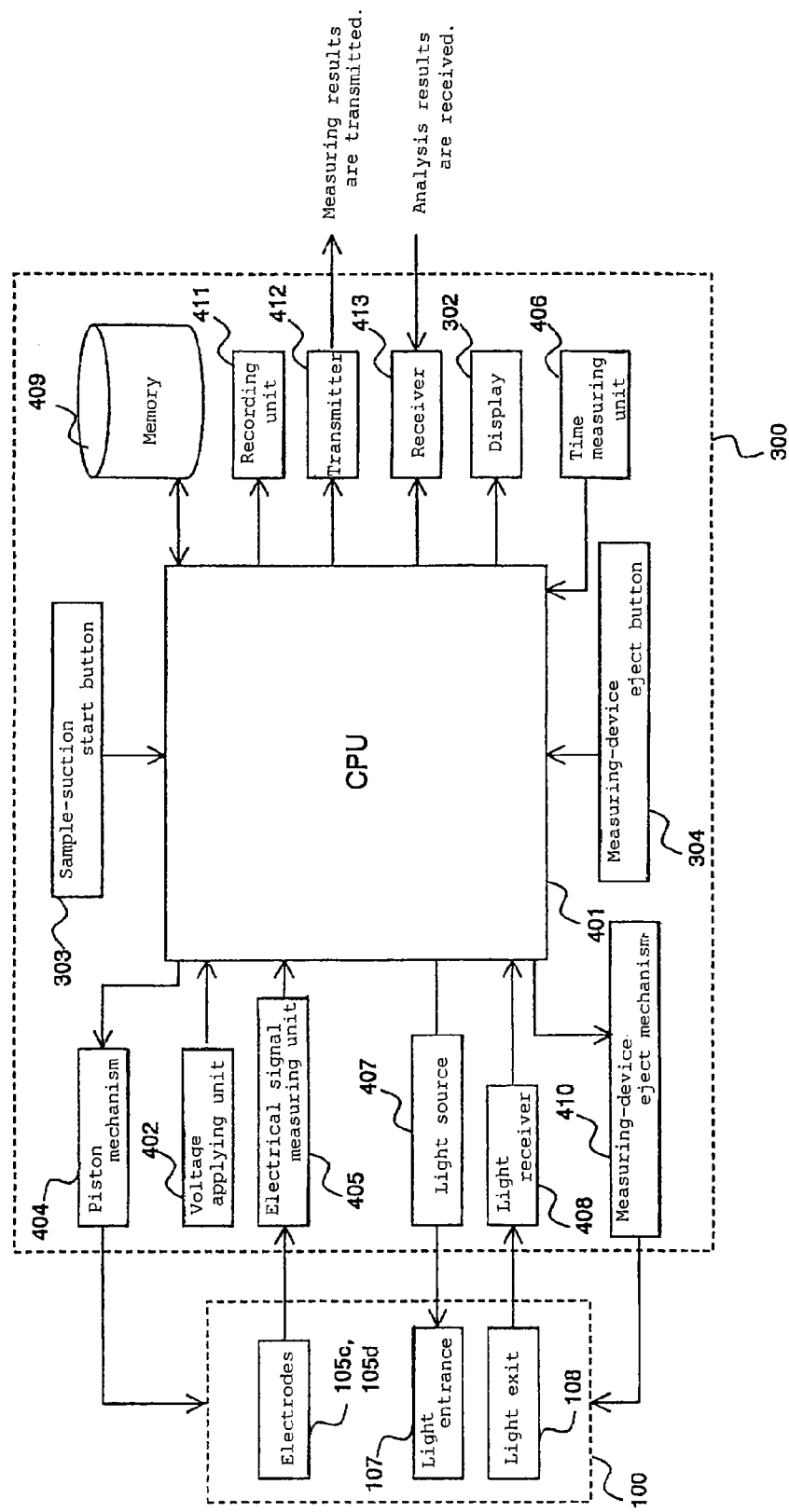
FIG. 5 is a block diagram showing the configuration of the measuring apparatus of the present invention illustrated in FIG. 4.
Figure 6:
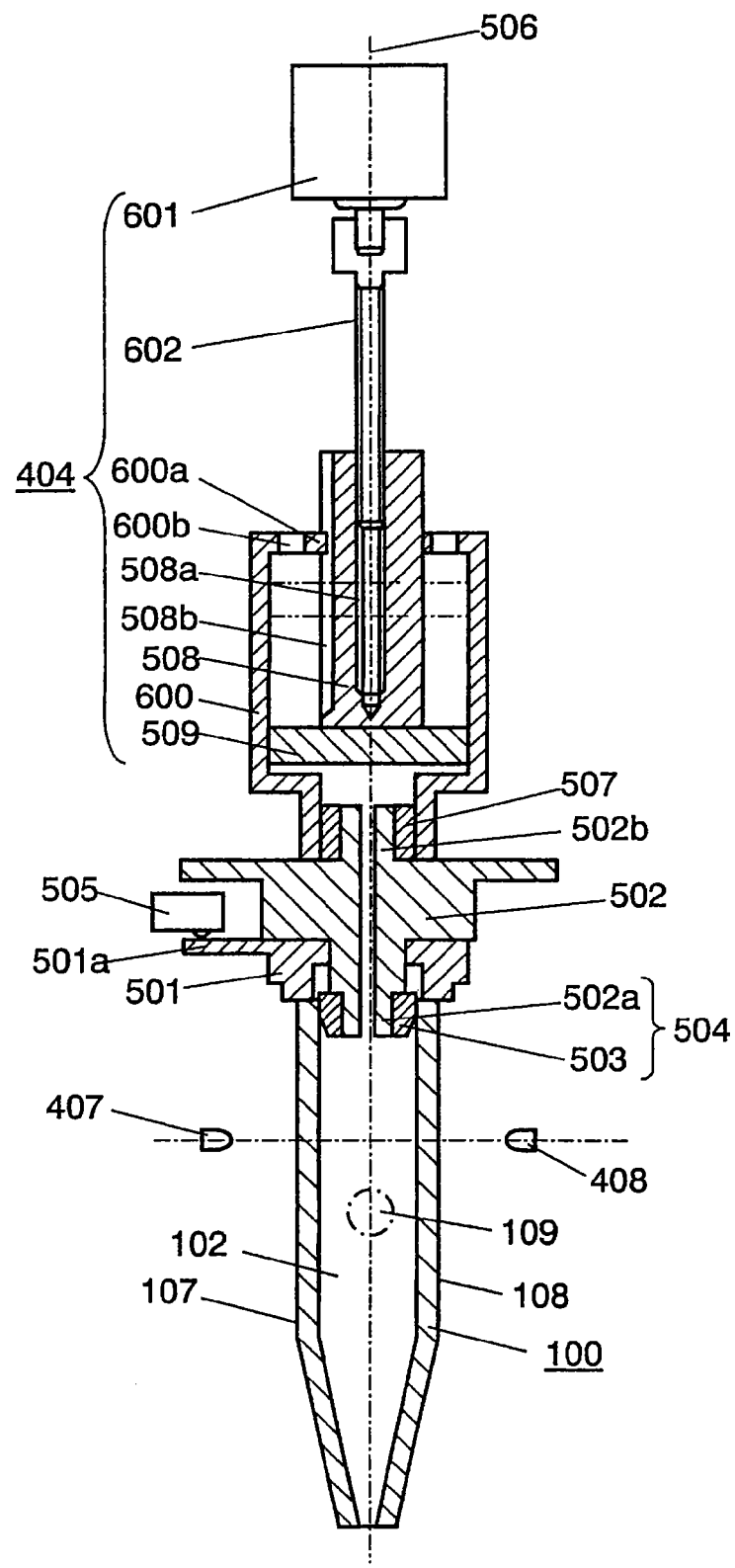
FIG. 6 is a cross-sectional view showing the structure of the same measuring apparatus into which the measuring device is inserted.
Figure 7:
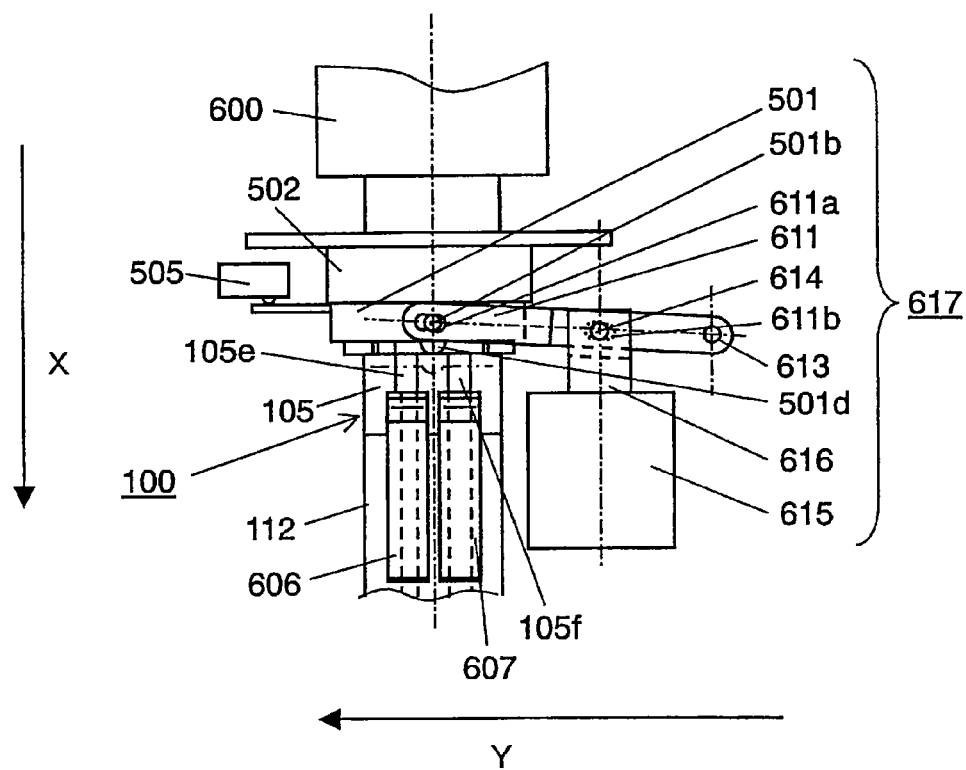
FIG. 7 is a front view of a measuring-device eject mechanism of the same measuring apparatus.
Figure 8:
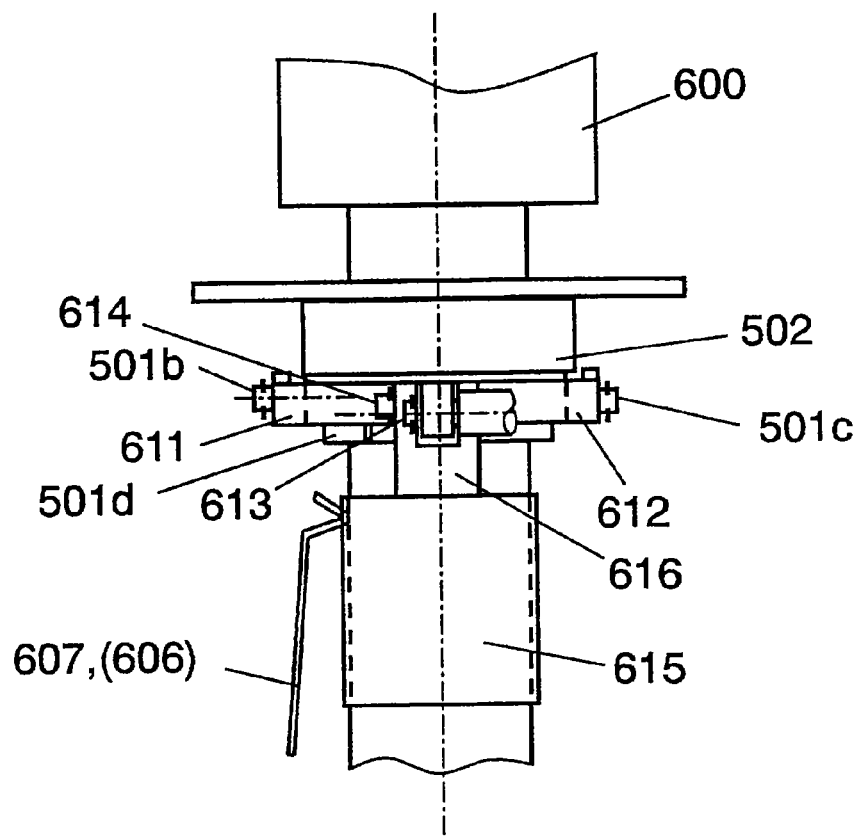
FIG. 8 is a side view of the measuring-device eject mechanism of the same measuring apparatus.

An embodiment of the measuring apparatus of the present invention is hereinafter described with reference to drawings. The structure of the measuring apparatus according to this embodiment is described by using FIGS. 4 to 8. FIG. 4 is a perspective view of the measuring apparatus of this embodiment, and FIG. 5 is a block diagram showing the configuration of the measuring apparatus of this embodiment. FIG. 6 is a schematic cross-sectional view showing the main structure of the measuring apparatus of this embodiment into which the measuring device is inserted. Also, FIG. 7 is a front view of a measuring-device eject mechanism of the measuring apparatus of this embodiment, and FIG. 8 is a side view of the same measuring-device eject mechanism.

As illustrated in FIG. 4, a measuring apparatus 300 of this embodiment has a measuring-device mounting part 301 for mounting the measuring device 100 in the measuring apparatus 300. The measuring-device mounting part 301 has a device mounting port (not shown) for detachably connecting with the sucking port 104 of the measuring device 100. It also has terminals (not shown) for electrically connecting with the connecting parts 105e and 105f. There is also a display 302 which displays measurement results, a sample-suction start button 303, and a measuring-device eject button 304.

As illustrated in FIG. 5, the measuring apparatus 300 contains: a light source 407 for emitting light which will enter the optical measurement part of the measuring device 100 mounted in the measuring-device mounting part 301; a light receiver 408, which is a light receiving unit for receiving the light that has exited from the optical measurement part; a voltage applying unit 402 for applying a voltage to the electrodes 105c and 105d of the measuring device 100; and an electrical signal measuring unit 405 for measuring the electrical signal from the electrodes 105c and 105d.

The measuring apparatus 300 further contains: a CPU 401 which is a processor for detecting or quantifying an analyte contained in a sample based on at least one of the light received by the light receiver 408 and the electrical signal measured by the electrical signal measuring unit 405; and a piston mechanism 404 which is a suction unit for sucking the sample into the sample holding part 102 of the measuring device 100.

In this embodiment, the light source 407 can be, for example, a semiconductor laser which emits light with a wavelength of 650 nm. Instead of this, for example, a light emitting diode (LED) may be used.

In this embodiment, assuming that measurements are made by turbidimetric immunoassay, 650 nm is selected as the wavelength of light emitted and received, but this wavelength can be selected appropriately according to the measurement method and the measuring object.

In this embodiment, the light receiver 408 can be, for example, a photodiode. Instead of this, the light receiver 408 may be, for example, a charge-coupled device (CCD) or a photomultimeter. Also, in this embodiment, the piston mechanism 404 is configured such that the piston is operated by a linear stepper motor.

The measuring apparatus 300 further contains a memory 409, which is a storage device that stores data on a first calibration curve representing the relation between the concentration of human albumin, which is the first analyte, and the intensity of light received by the light receiver 408 and data on a second calibration curve representing the relation between the concentration of glucose, which is the second analyte, and the electrical signal measured by the electrical signal measuring unit 405.

The measuring device 100 is inserted into the measuring apparatus 300 through the measuring-device mounting part 301 (see FIG. 4). As illustrated in FIG. 6, the measuring device 100 pushes a slide member 501 upward in FIG. 6, and the measuring device 100 mates with a device mounting port 504, which is composed of a protrusion 502a that protrudes from a frame member 502 for mounting the device and a sealing member 503 that is fitted to the outer periphery of the protrusion 502a for mounting the device. The protruding device mounting port 504 is inserted into the sucking port 104, so that a push protrusion 501a of the slide member 501 presses a switch 505 for detecting insertion of the measuring device. When the measuring-device insertion detecting switch 505 is pressed, completion of the mounting of the measuring device 100 into the measuring apparatus 300 is detected.

The shapes of the outer edge of the device mounting protrusion 502a and the outer edge of the device mounting sealing member 503, i.e., the shapes of their cross-sections in the direction perpendicular to a longitudinal central axis 506 are similar to the shape of the inner face of the sucking port 104 of the measuring device 100. The size of the outer edge of the device mounting sealing member 503 is made slightly larger than the size of the sucking port 104 of the measuring device 100, thereby enhancing the adhesion between the device mounting sealing member 503 and the sucking port 104 and preventing leakage of air in the joint thereof. Also, the device mounting sealing member 503 is made of, for example, an elastic material such as isoprene rubber, fluorocarbon rubber, silicone rubber, or Teflon (registered trademark) coating rubber. The sealing member may be linear or the protruding device mounting port 504 itself may be composed of an elastic material.

The frame member 502 has a protrusion 502b for mounting a cylinder on the side opposite to the device mounting protrusion 502a. A sealing member 507 for mounting a cylinder, made of the same material as the device mounting sealing member 503, is fitted around the cylinder mounting protrusion 502b to provide gas tightness. A cylinder 600, which contains a piston 509 to which a piston rod 508 is fixed, is fitted to the cylinder mounting protrusion 502b of the frame member 502 with the cylinder mounting sealing member 507 therebetween to provide gas tightness.

The piston rod 508 has a female thread 508a in the center thereof, and has a key groove 508b on the outer periphery in the longitudinal direction. The key groove 508b is engaged with a protrusion 600a, which is at the opposite end of the cylinder 600 from the joint with the cylinder mounting sealing member 507, so that the piston rod 508 can move linearly without rotation.

Also, a male thread 602 fixed to the rotational shaft of a motor 601 is screwed to the female thread 508a of the piston rod 508, so that due to the rotation of the male thread 602 caused by the rotation of the motor 601, the piston rod 508 having the female thread 508a screwed to the male thread 602 can move linearly along the longitudinal central axis 506 upward and downward in the figure.

At the end of the cylinder 600 with the protrusion 600a, there is a hole 600b for releasing air inside the cylinder 600 upon movement of the piston 509. The cylinder 600 having the piston 509 to which the piston rod 508 is fixed, the male thread 602 screwed to the female thread 508a of the piston rod 508, and the motor 601 to which the male thread 602 is fixed constitute the piston mechanism 404, which is the suction unit for sucking a sample into the measuring device 1.

Thus, with the measuring device 100 mounted in the measuring apparatus 300 such that the sucking port 104 of the measuring device 100 is connected to the measuring apparatus 300, a sample can be easily supplied to the sample holding part 102 of the measuring device 100 by sucking the sample from the sample supply inlet 104 of the measuring device 100 using the piston mechanism 404 serving as the suction unit.

Also, the measuring apparatus 300 includes the light source 407 for emitting light that will enter the optical measurement part, which is composed of the light entrance of the second face 107 and the light exit of the third face 108 of the measuring device 100 mounted in the measuring apparatus 300, and the light receiver 408 serving as the light receiving unit for receiving light that has exited from the optical measurement part. The light emitted from the light source 407 passes through the light entrance of the second face 107 of the measuring device 1, the sample supplied to the sample holding part 102 of the measuring device 100, and the light exit of the third face 108 of the measuring device 100, and is received by the light receiver 408. The light receiver 408 produces an electrical signal corresponding to the intensity of the light it received. It is preferable to determine the positions of the light source 407 and the light receiver 408 so that in the optical path of light which is emitted from the light source 407 and received by the light receiver 408, the spots of light passing through the light entrance and the light exit of the measuring device 100 are positioned away from the joints between the first member 201 and the second member 202 of the measuring device 100.

Also, as illustrated in FIGS. 7 and 8, the slide member 501 has push pins 501b and 501c, for example, on the faces corresponding to the opposing first face 105 and fourth face 106 of the measuring device 100, respectively. FIG. 8 is a view seen from the direction of the arrow Y in FIG. 7. Drive levers 611 and 612 have, at their ends, long holes 611a and 612a (not shown) to which the push pins 501b and 501c are slidably engaged, respectively. The drive levers 611 and 612 are installed so as to swing on a fixed fulcrum shaft 613. The drive levers 611 and 612 are shaped like substantial Z and reversed substantial Z, respectively, when seen from the direction of the arrow X. The drive levers 611 and 612 are joined so as to face each other on the opposite side of the long holes 611a and 612a formed at the ends thereof, while the ends of the drive levers 611 and 612 with the long holes 611a and 612a are apart from each other such that they engage with the push pins 501b and 501c of the slide member 501.

At the portion where the drive levers 611 and 612 are joined so as to face each other, long holes 611b and 612b (not shown) are formed at the same position of the drive levers 611 and 612 so that they align together. They are coupled to a plunger 616 of a solenoid 615 by means of working pins 614 engaged in the long holes 611b and 612b. A measuring-device eject mechanism 617 is composed of the slide member 501, the drive levers 611 and 612 which swing on the fulcrum shaft 613, the working pins 614, and the solenoid 615 having the plunger 616 which swings the drive levers 611 and 612.

Upon completion of a measurement of a sample by the measuring apparatus 300, a current is supplied to the solenoid 615. As a result, the plunger 616 is sucked and the drive levers 611 and 612 are swung via the working pins 614 counter-clockwise in the figure. Due to the swing of the drive levers 611 and 612, the push pins 501b and 501c of the slide member 501 are pushed via the long holes 611a and 612a of the drive levers 611 and 612, so that the slide member 501 is moved downward in the figure. Meanwhile, the slide member 501 has push projections 501d at least at two locations near the push pins 501b and 501c, and the push projections 501d are in contact with the end of the measuring device 100. When the slide member 501 is moved, the measuring device 100 is moved downward in the figure. As a result, it is possible to disconnect the measuring device 100 from the device mounting port 504 and detach the measuring device 100 from the measuring apparatus 300.

3. Measuring Method

Next, the method of measuring an analyte in a sample by using the measuring device 100 and the measuring apparatus 300 of this embodiment is described with reference to FIGS. 4 to 8. In the following description, urine is used as the sample.

First, the sucking port 104 of the measuring device 100 is joined to the device mounting port 504 in the measuring-device mounting part 301 of the measuring apparatus 300, in order to mount the measuring device 100 in the measuring-device mounting part 301. As a result, the connecting parts 105e and 105f come into contact with two terminals 606 and 607 inside the measuring-device mounting part 301 to electrically connect the two electrodes 105c and 105d of the measuring device 100 with the two terminals, respectively.

At this time, the measuring-device insertion detecting switch 505, which is a microswitch inside the measuring apparatus 300, is turned on. As a result, the CPU 401, which functions as a controlling unit, detects the insertion of the measuring device 100 and a voltage (e.g., a voltage such that the electrode 105c is at +0.2 V relative to the electrode 105d) is applied between the two electrodes 105c and 105d of the measuring device 100 by the voltage applying unit 402.

Next, the measuring device 100 is immersed in, for example, urine collected in a portable container such as a urine container or paper cup placed in a toilet bowl, up to at least the position of the first reference line 110, in order to immerse the sample supply inlet 103 and the two electrodes 105c and 105d of the measuring device 100 in the urine. When the urine comes into contact with the electrodes 105c and 105d, a current flows between the two electrodes, and a resulting change in electrical signal is detected by the electrical signal measuring unit 405.

Upon the detection, the voltage applied by the voltage applying unit 402 is switched to a different voltage (e.g., a voltage such that the electrode 105c is at +0.5 V relative to the electrode 105d). Also, upon the detection, the CPU 401 makes a time measuring unit 406, which is a timer, start time measurement.

When the CPU 401 determines from the signal sent from the time measuring unit 406 that a predetermined time (e.g., 15 seconds) has passed, electrical signal such as the current flowing between the electrode 105c and the electrode 105d is measured by the electrical signal measuring unit 405. The CPU 401 converts the measured electrical signal into glucose concentration in the urine by reading the second calibration curve representing the relation between electrical signal and glucose (urine sugar) concentration stored in the memory 409 and referring to it. Glucose oxidase, which is an enzyme, and an osmium complex, which is an electron mediator, are carried on the surface of the pair of electrodes 105c and 105d. Hence, a current corresponding to the glucose concentration in the sample flows between the pair of electrodes 105c and 105d as an electrical signal, which is measured by the electrical signal measuring unit 405. The glucose concentration in the urine sample can be determined as described above.

The glucose concentration obtained is displayed on the display 302. Upon the display of glucose concentration on the display 302, the user can know the completion of the glucose concentration measurement. After the completion of the glucose concentration measurement, the sample supply inlet 103 can be pulled out of the urine.

Also, when the electrical signal measuring unit 405 detects a change in electrical signal upon contact of the urine with the two electrodes 105c and 105d, the CPU 401 determines that the sample supply inlet 103 has been immersed in the sample and makes the piston mechanism 404 function. As a result, the piston in the piston mechanism 404 moves and a predetermined amount (e.g., 3 mL) of the urine is sucked from the sample supply inlet 103 of the measuring device 100 into the sample holding part 102.

This makes it possible to prevent the sample from being mistakenly sucked before the sample supply inlet is immersed in the sample and reduce the workload of the user. Also, by keeping the piston at the position when the sample is sucked, the urine is held in the sample holding part 102 and prevented from leaking from the sample supply inlet 103 or being sucked into the piston mechanism 404.

Alternatively, the user may press the sample-suction start button 303 to operate the piston mechanism 404 when having confirmed that at least the sample supply inlet 103 is immersed in the urine, in order to suck the urine into the sample holding part 102.

When the two electrodes 105c and 105d come out of the urine during the operation of the piston mechanism 404, the electrical signal measuring unit 405 redetects a change in electrical signal, so the piston mechanism 404 is stopped upon the detection. This makes it possible to prevent the sample in the sample holding part 102 from being continuously sucked by the piston mechanism 404 when the two electrodes 105c and 105d are out of the urine and thus prevent the sample from mistakenly entering the piston mechanism 404.

The urine supplied to the sample holding part 109 dissolves the dry reagent carried on the reagent holding part 109, i.e., anti-human albumin antibody, so that an immune reaction between the antigen in the urine, i.e., human albumin, and the anti-human albumin antibody proceeds. Upon completion of the supply of sample to the sample holding part 102, the CPU makes the time measuring unit 406, which is a timer, start time measurement.

When the CPU 401 determines from the signal sent from the time measuring unit 406 that a predetermined time (e.g., 2 minutes) has passed from the completion of the supply of sample to the sample holding part 102, the CPU 401 makes the light source 407 emit light.

The light emitted by the light source 407 passes through the light entrance 107 of the measuring device 100 and enters the sample holding part 102. It then passes through the urine and scatters. The light having exited from the light exit 108 is received by the light receiver 408 disposed in the measuring apparatus 300 for a predetermined time (e.g., 3 minutes).

The CPU 401 converts the intensity of the outgoing light received by the light receiver 408 into human albumin concentration by reading the first calibration curve representing the relation between outgoing light intensity and human albumin concentration stored in the memory 409 and referring to the first calibration curve.

The human albumin concentration obtained is displayed on the display 302. Then, the user can know the completion of the human albumin concentration measurement. Preferably, the urine sugar concentration and human albumin concentration obtained are stored in the memory 409 together with the time measured by the time measuring unit 406.

Further, the urine sugar concentration and human albumin concentration obtained can be recorded onto a recording medium such as an SD card by a recording unit 411. When the measurement results are stored in a detachable recording medium, they can be readily taken out of the measuring apparatus 300. It is thus possible to bring or mail the recording medium to an analytical laboratory for analysis.

Also, the urine sugar concentration and human albumin concentration obtained can be transmitted from the measuring apparatus 300 to outside by a transmitter 412. Thus, the measurement results can be transmitted to an analytical division in a hospital, analytical service, etc, so that they can be analyzed by the analytical division, analytical service, etc. It is therefore possible to shorten the time required from measurement to analysis.

Further, there is also a receiver 413 for receiving the results of analysis by the analytical division, analytical service, etc. It is therefore possible to promptly feed back the results of analysis to the user.

Lastly, when the user presses the measuring-device eject button 304, a measuring-device eject mechanism 410 functions and causes the piston in the piston mechanism 404 to move. As a result, the urine in the sample holding part 102 is discharged from the sample supply inlet 103 into a toilet bowl or a container such as a paper cup, and then the measuring device 100 is automatically detached from the measuring apparatus 300.

The measuring device 100 may be manually detached from the measuring-device mounting part 301 by the user, without providing the measuring device with such a mechanism for detaching the device and discharging the sample.

As described above, by supplying a sample once to the sample holding part 102, it is possible to perform optical and electrochemical measurements of the sample by using one measuring device 100.

Also, by providing the reagent holding part 109 on the inner surface of the housing 101 of the measuring device 100 and providing the electrodes 105c and 105d on the outer surface of the housing 101, the reagent necessary for the optical measurement is prevented from diffusing into the electrodes and thus affecting the electrochemical measurement. It is thus possible to measure a plurality of test items promptly and correctly.

In the above description, an exemplary embodiment of the present invention has been described. However, the shape of the measuring device 100 is not limited to the one described in the above embodiment as long as the requirements of the present invention are satisfied and the effects of the present invention can be obtained.

Figure 9:
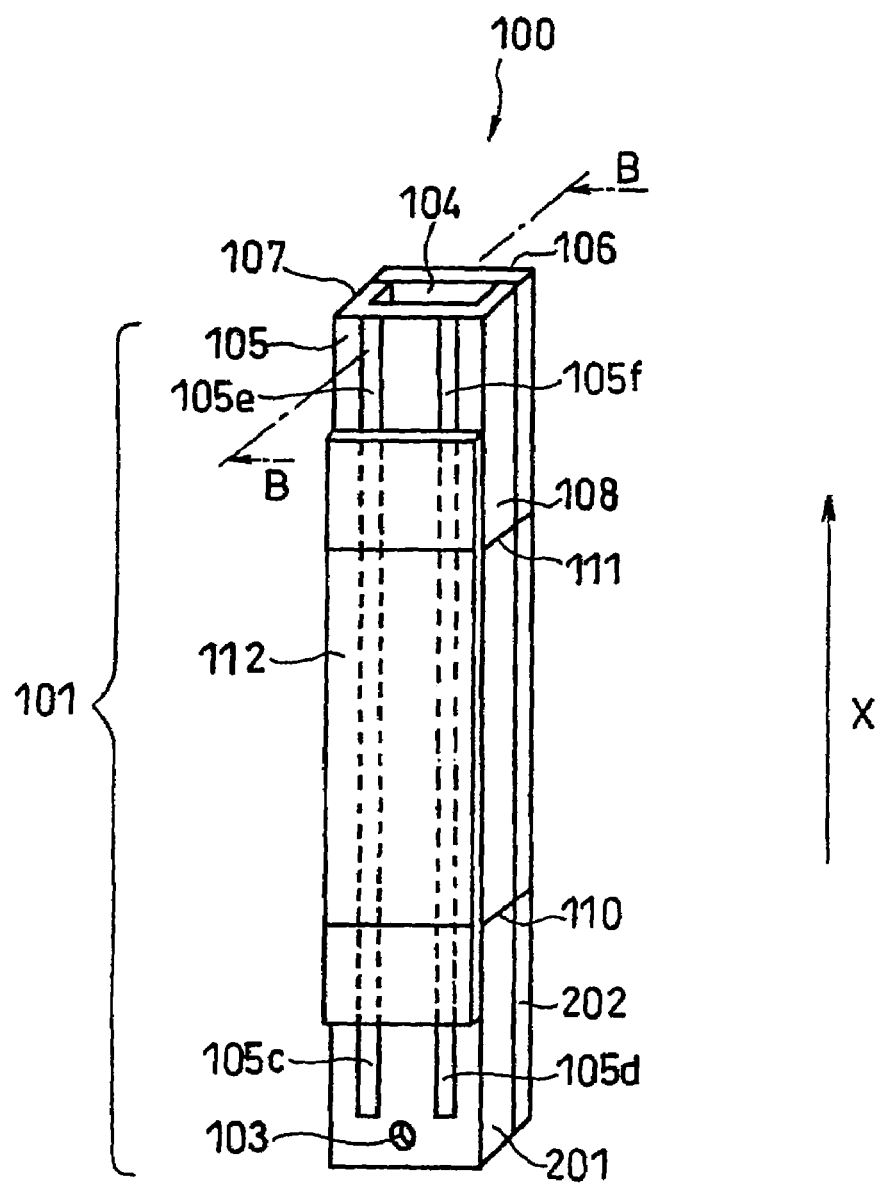
FIG. 9 is a perspective view showing the structure of one modified example of the measuring device according to the present invention.
Figure 10:
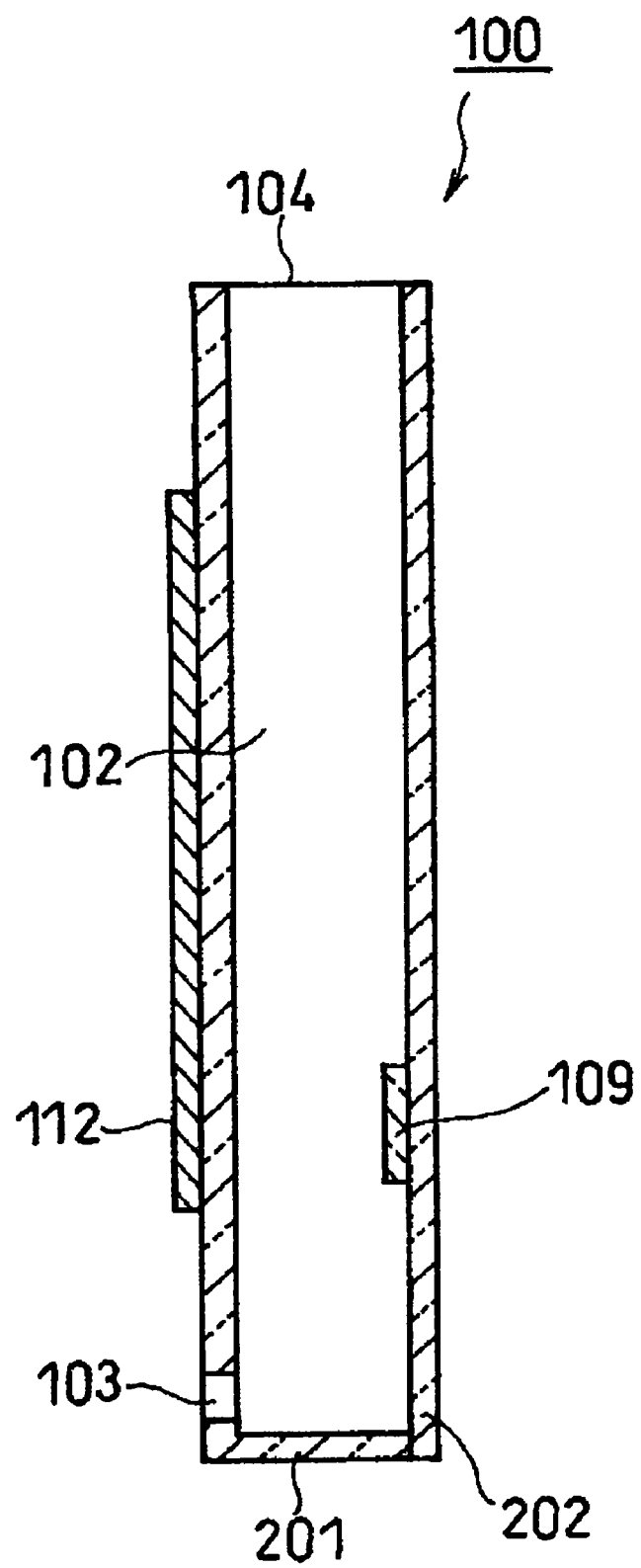
FIG. 10 is a cross-sectional view of the B-B part of FIG. 6.

FIG. 9 is a perspective view showing a first modified example of the measuring device of the above embodiment, and FIG. 10 is a cross-sectional view of the B-B part of FIG. 9. The same constituent elements as those in FIGS. 1 and 2 are given the same reference characters and explanations thereof are omitted.

As illustrated in FIG. 9, a measuring device 100 of this modified example includes a housing 101 with a bottom, which is in the shape of a hollow rectangular parallelepiped having therein a space serving as a sample holding part 102. The housing 101 has a sample supply inlet 103 in a first face 105.

The housing 101 of this modified example includes a member (first member) 201 having a first face 105, a second face 107, a third face 108, and a bottom, and a back plate (second member) 202.

Figure 11:
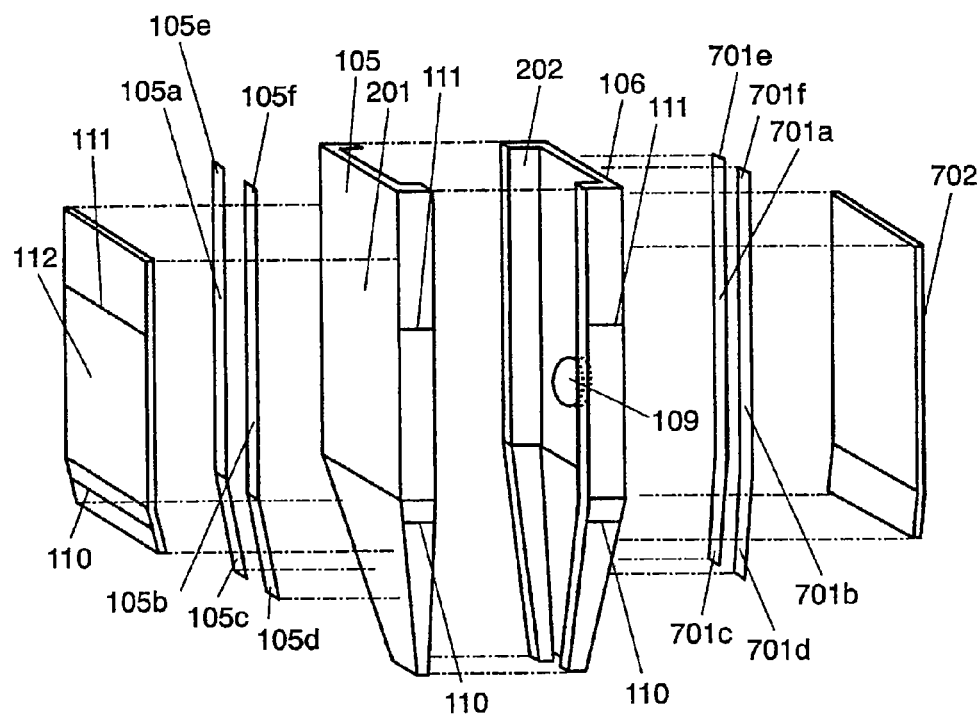
FIG. 11 is an exploded perspective view showing the structure of another modified example of the measuring device according to the present invention.

Also, in this embodiment, the pair of electrodes 105c and 105d has been described, but this is not to be construed as limiting, and the number of electrodes and pairs can be changed as appropriate, if necessary. A second modified example of the measuring device of the above embodiment having a plurality of pairs of electrodes is briefly described with reference to FIG. 11. In FIG. 11, the elements corresponding to the constituent elements in FIG. 1 and FIG. 2 are given the same reference characters as those in FIG. 1 and FIG. 2.

In FIG. 11, a first face 105 is provided with conductive parts 105a and 105b for forming a pair of electrodes 105c and 105d and corresponding connecting parts 105e and 105f. The first face 105 is opposed to a fourth face 106 whose outer surface is provided with conductive parts 701a and 701b for forming a pair of electrodes 701c and 701d and corresponding connecting parts 701e and 701f.

A cover 702 is disposed so as to define the areas of the electrodes 701c and 701d in the same manner as a cover 112 attached to the first face 105, and detailed explanation thereof is omitted. It is preferable to use respective pairs of electrodes (two pairs of electrodes in this description) to quantify different analytes. For example, one pair of electrodes 105c and 105d may be used to measure the salt concentration by conductivity, and the other pair of electrodes 701c and 701d may be used to measure urine sugar. Further, in the case of using an additional pair of electrodes, for example, creatinine may be additionally measured. Combinations of analytes are not to be limited to these examples, and substances that need to be measured may be selected as appropriate.

Also, in this embodiment, the method of disposing the insulating resin cover 112 on the conductive parts 105a and 105b so as to expose both ends of the conductive parts 105a and 105b in order to form the electrodes 105c and 105d and the connecting parts 105e and 105f has been described, but this is not to be construed as limiting.

Figure 12:
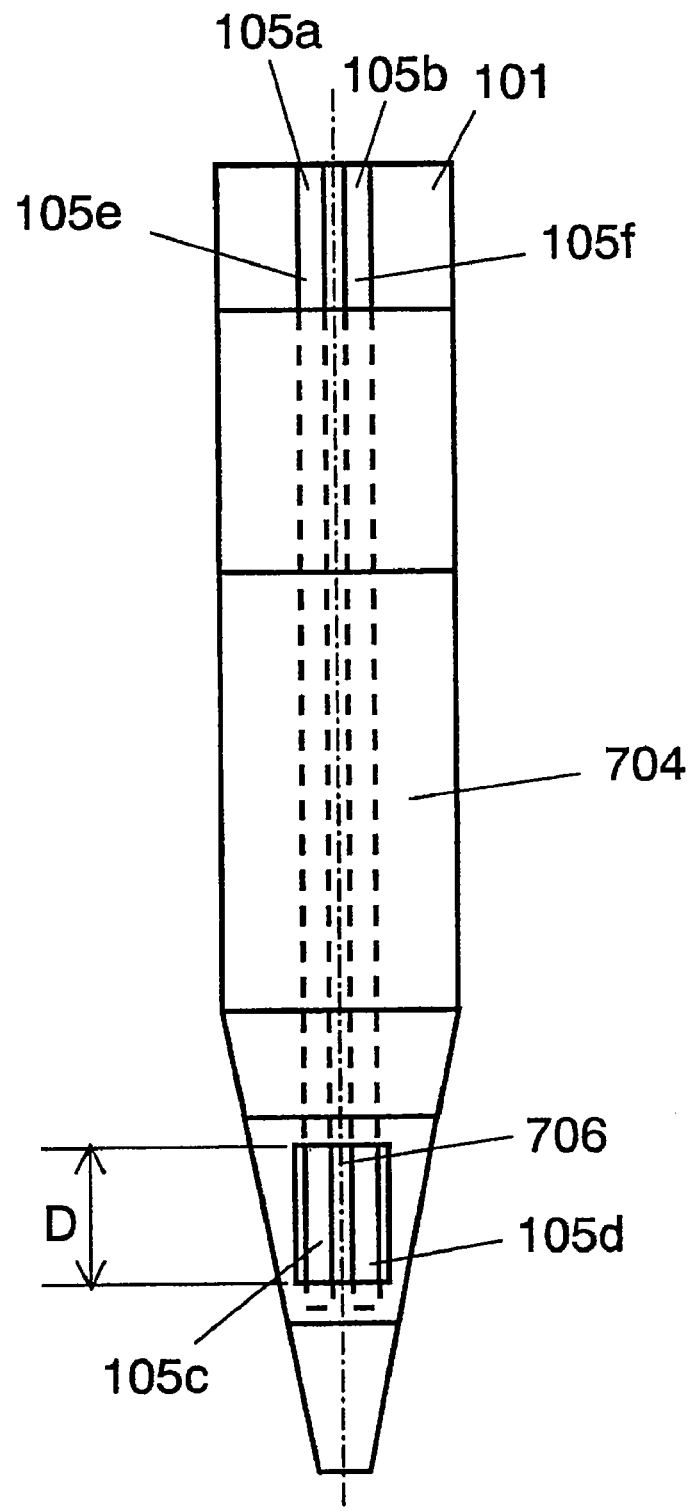
FIG. 12 is a front view of still another modified example of the measuring device according to the present invention.

A third modified example of the measuring device of the above embodiment is described. As illustrated in FIG. 12, a cover 704 has an opening 706 at the position corresponding to electrodes 105c and 105d, and the opening 706 is formed so as to have a length D such that the length dimension of the pair of electrodes 105c and 105d exposed from the opening 706 is a predetermined dimension. It is also possible to use a method of attaching the cover 704 with the opening 706 onto the conductive parts 105a and 105b to form the pair of electrodes 105c and 105d and connecting parts 105e and 105f.

By using the cover 704 of such shape, even if the bonding position of the cover 704 is slightly displaced, the areas of the exposed parts of the electrodes 105c and 105d become constant, and accurate measurements are possible. In this example, the shape of the opening is rectangular, but it may be circular, triangle, polygonal, or oval.

Figure 13:
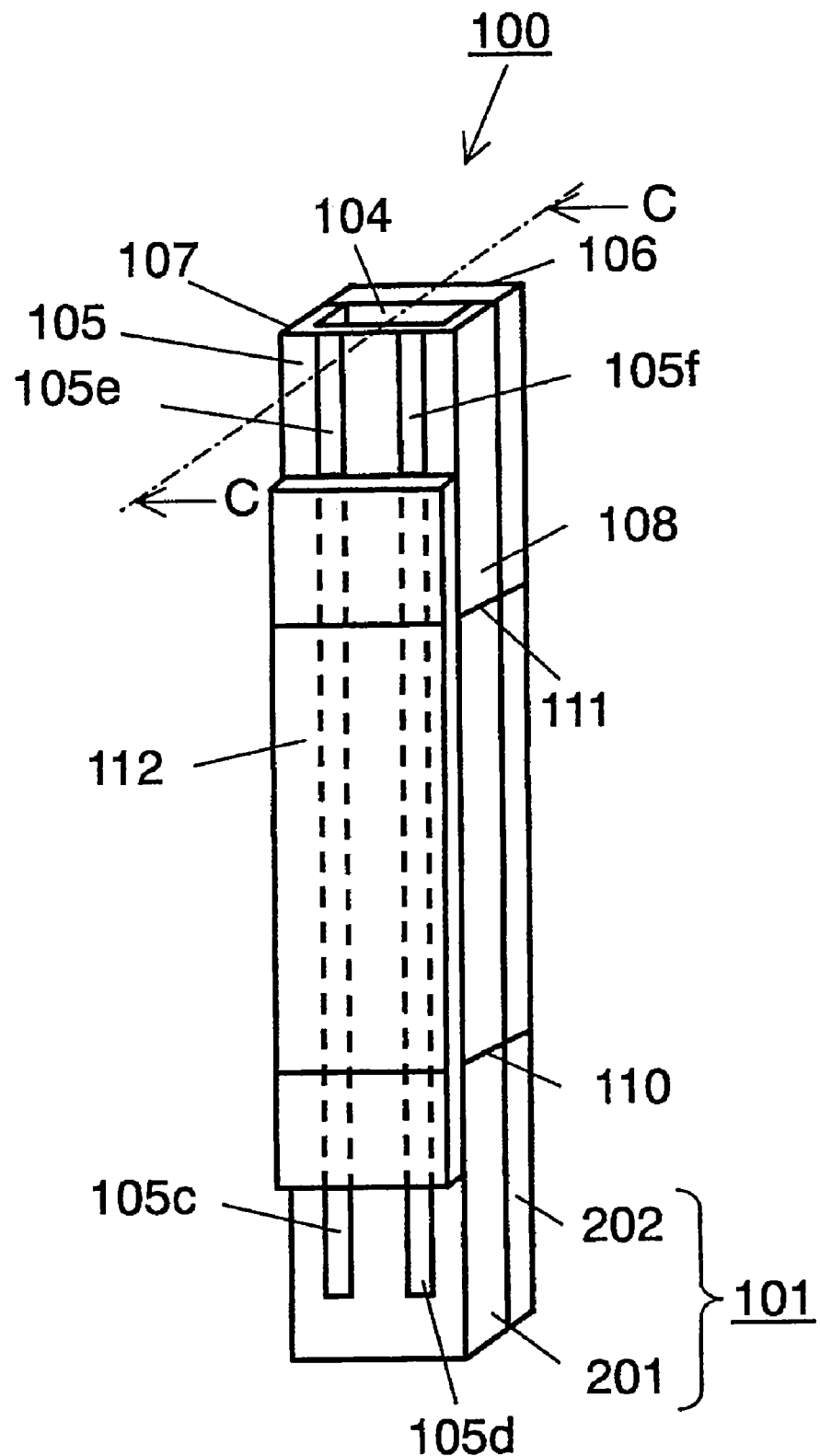
FIG. 13 is a perspective view showing the structure of still another modified example of the measuring device according to the present invention.
Figure 14:
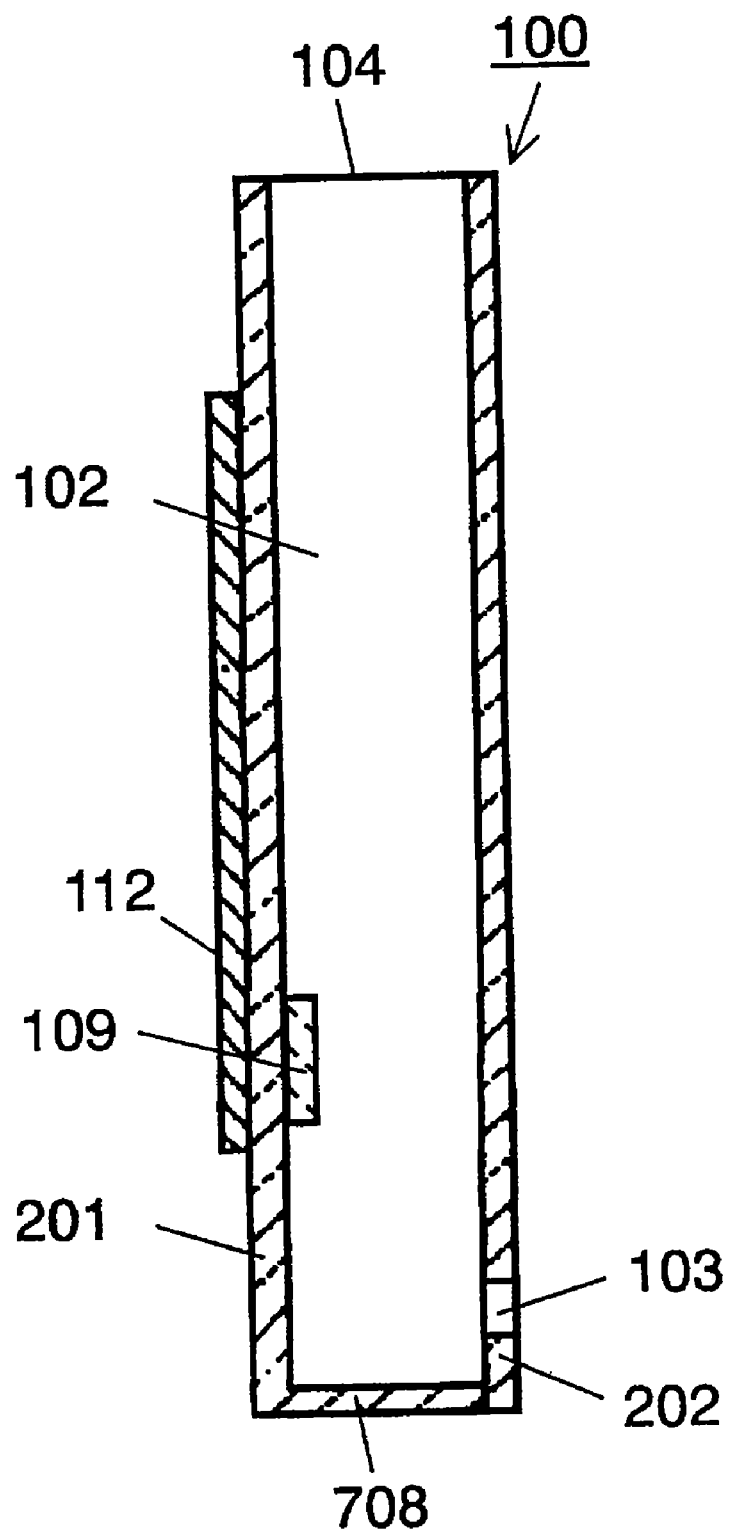
FIG. 14 is a cross-sectional view of the B-B part of FIG. 13.

Also, a fourth modified example of the measuring device of the above embodiment is described with reference to FIG. 13 and FIG. 14. In FIG. 13 and FIG. 14, the elements corresponding to the constituent elements in FIG. 1 and FIG. 2 are given the same reference characters as those in FIG. 1 and FIG. 2.

In FIG. 13 and FIG. 14, a measuring device 100 includes a housing 101 with a bottom, which is in the shape of a hollow rectangular parallelepiped having therein a space serving as a sample holding part 102. The housing 101 is composed of a first member 201 with a first face 105, a second face 107, a third face 108, and a bottom 708, and a second member 202 which is a back plate constituting a fourth face 106.

In the housing 101, a pair of electrodes 105c and 105d is formed on the first face 105, a sample supply inlet 103 is formed in the fourth face 106 which is opposed to the first face 105, and a reagent holding part 109 for holding a reagent is formed on the inner face of the first member 201, i.e., the face forming a sample holding part 102.

In the first member 201, a pair of conductive parts 105a and 105b is formed on the outer surface of the first face 105, and a cover 112 is attached such that the electrodes 105c and 105d and connecting parts 105e and 105f are formed at opposite ends of the conductive parts 105a and 105b, respectively. Also, a first reference line 110 and a second reference line 111 are formed on the housing 101 and the cover 112.

Also, in the description of the above embodiment, the reagent holding part 109 was formed by applying an aqueous solution containing a reagent for optical measurement and drying it. Instead, it is also possible to use a method of impregnating a porous carrier made of glass fiber, filter paper, etc., with a solution of a reagent, drying or freeze drying it to carry the reagent, and attaching the porous carrier to the bottom of the recess of the first member 201 to carry the reagent.

In the above embodiment, the method of forming the conductive parts 105a and 105b, the electrodes 105c and 105d, and the connecting parts 105e and 105f by sputtering or vapor deposition was described. Instead, it is possible to use a method of attaching a metal ribbon to the outer surface of the first member 201, a method of printing an ink containing metal or carbon onto the outer surface of the first member 201, etc.

Further, in the above embodiment, upon the detection of the contact of the urine with the two electrodes 105c and 105d, the voltage value was changed, but such changing is not always necessary. If a voltage necessary for measurement is applied before a sample is supplied, the voltage can be continuously applied after the supply.

In the above embodiment, light was irradiated after a predetermined time had passed from the completion of the supply of the urine to the sample holding part, but the irradiation may be started simultaneously with the detection of the sample.

INDUSTRIAL APPLICABILITY

The present invention can provide a measuring device, a measuring apparatus, and a measuring method capable of measuring a plurality of test items promptly and accurately by performing optical and electrochemical measurements of a sample using a simple configuration. Therefore, the present invention is useful in the medical and medical related test fields, in particular, for measuring urine specimens.

The invention claimed is:

1. A measuring device for analyzing an analyte contained in a sample, comprising:
    a hollow housing;
    a sample holding part provided inside said housing for holding the sample;
    a sample supply inlet provided for said housing so as to communicate with said sample holding part;
    an optical measurement part provided for said sample holding part for making an optical measurement;
    a reagent holding part provided for said sample holding part for holding a reagent for said optical measurement; and
    at least one electrode provided on an outer surface of said housing,
    wherein said housing has a first reference line that indicates a position up to which said housing is to be immersed in said sample.

2. A measuring device for analyzing an analyte contained in a sample, comprising:
    a hollow housing;
    a sample holding part provided inside said housing for holding the sample;
    a sample supply inlet provided for said housing so as to communicate with said sample holding part;
    an optical measurement part provided for said sample holding part for making an optical measurement;
    a reagent holding part provided for said sample holding part for holding a rea2ent for said optical measurement; and
    at least one electrode provided on an outer surface of said housing,
    wherein said housing has a second reference line that indicates the amount of said sample to be supplied to said housing.

3. A method for measuring a first analyte and a second analyte contained in a sample by using a measuring device,
    said measuring device including a hollow housing; a sample holding part provided inside said housing for holding the sample; a sample supply inlet provided for said housing so as to communicate with said sample holding part; an optical measurement part provided for said sample holding part for making an optical measurement; a reagent holding part provided for said sample holding part for holding a reagent for said optical measurement; and electrodes provided on an outer surface of said housing,
    said method comprising the steps of:
    (A) applying a voltage to said electrodes of said measuring device;
    (B) measuring an electrical signal from said electrodes;
    (C) sucking said sample into said sample holding part through said sample supply inlet;
    (D) detecting or quantifying said second analyte based on said electrical signal measured in said step (B);
    (E) irradiating said sample held in said sample holding part with light through said optical measurement part;
    (F) measuring light which has originated from said irradiation of light and exited from said sample holding part through said optical measurement part; and
    (G) detecting or quantifying said first analyte based on said light measured in said step (F).

4. The measuring method in accordance with claim 3, wherein a change in said electrical signal is detected in said step (B), and
    based on said detection, said step (C) is automatically performed.

5. The measuring method in accordance with claim 3, wherein while said step (C) is being performed, said step (B) is performed,
    a change in said electrical signal is detected in said step (B), and
    based on said detection, the sucking of said sample is automatically stopped.

* * * * *

UNITED STATES PATENT AND TRADEMARK OFFICE
CERTIFICATE OF CORRECTION

| | | |
|---|---|---|
| PATENT NO. | : 7,646,474 B2 | Page 1 of 1 |
| APPLICATION NO. | : 11/995473 | |
| DATED | : January 12, 2010 | |
| INVENTOR(S) | : Takahiro Nakaminami et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Delete "This patent is subject to a terminal disclaimer.".

In Column 20, line 21 (Claim 2), please delete, "part for holding a rea2ent", and insert --part for holding a reagent--.

Signed and Sealed this

Fifth Day of October, 2010

David J. Kappos
*Director of the United States Patent and Trademark Office*